United States Patent
Abate et al.

(10) Patent No.: US 7,967,576 B2
(45) Date of Patent: Jun. 28, 2011

(54) AUTOMATISED ASSEMBLY OPERATING UNIT IN PARTICULAR FOR AEROSOL APPLIANCES

(75) Inventors: Riccardo Abate, S. Martino Della Battaglia (IT); Luigi Abate, S. Martino Della Battaglia (IT)

(73) Assignee: Flaem Nuova S.p.A., Martino Della Battaglia (Brescia) (IT)

( * ) Notice: Subject to any disclaimer, the term of this patent is extended or adjusted under 35 U.S.C. 154(b) by 1311 days.

(21) Appl. No.: 10/599,287

(22) PCT Filed: Mar. 24, 2005

(86) PCT No.: PCT/IT2005/000164
§ 371 (c)(1), (2), (4) Date: Sep. 25, 2006

(87) PCT Pub. No.: WO2005/096685
PCT Pub. Date: Oct. 13, 2005

(65) Prior Publication Data
US 2008/0190417 A1    Aug. 14, 2008

(30) Foreign Application Priority Data
Apr. 1, 2004 (IT) .............................. BS20040020 U

(51) Int. Cl.
*F04B 39/14* (2006.01)
(52) U.S. Cl. ... 417/360; 417/238; 417/363; 417/423.14; 128/204.18; 128/204.21
(58) Field of Classification Search ................. 417/238, 417/360, 363, 423.14; 128/200.14, 200.22, 128/204.18, 204.21, 205.18, 205.22; 392/380, 392/383, 384, 385; D24/110; D15/7
See application file for complete search history.

(56) References Cited

U.S. PATENT DOCUMENTS

| | | | | |
|---|---|---|---|---|
| 4,080,103 A | * | 3/1978 | Bird | 417/3 |
| 4,331,883 A | * | 5/1982 | Vitaloni | 307/150 |
| 4,389,166 A | * | 6/1983 | Harvey et al. | 417/234 |
| 4,949,715 A | | 8/1990 | Brugger | |
| D348,927 S | * | 7/1994 | Attolini | D24/110 |
| D376,199 S | * | 12/1996 | Rozek et al. | D24/110 |
| 6,152,134 A | * | 11/2000 | Webber et al. | 128/205.24 |
| 6,318,360 B1 | * | 11/2001 | Attolini | 128/200.14 |
| D454,393 S | * | 3/2002 | Lynch et al. | D24/110 |
| D480,093 S | * | 9/2003 | Attolini | D15/9 |
| 6,698,421 B2 | * | 3/2004 | Attolini | 128/200.14 |
| 6,926,503 B2 | * | 8/2005 | McGee et al. | 417/363 |

(Continued)

FOREIGN PATENT DOCUMENTS

DE    19949633    6/2001
EP    0265545    5/1988

*Primary Examiner* — Devon C Kramer
*Assistant Examiner* — Leonard J Weinstein
(74) *Attorney, Agent, or Firm* — McGlew and Tuttle, P.C.

(57) ABSTRACT

The invention concerns an operating unit to generate a flow of air under pressure in aerosol therapy equipment, comprising a pump group (12) powered by a motor and having a head (19), with an air inlet duct (22) complete with filter (24) and an air outlet duct (23). The pump group is enclosed in a body made up of two shells, top and bottom, (13, 14) which overlap and fit together on a transversal plane at the level of their edges. The shells forming the body receive and hold the air inlet duct (22) with filter, the air outlet duct (23) and a plate with socket and switch following their overlapping for automizable assembly of the group.

8 Claims, 4 Drawing Sheets

U.S. PATENT DOCUMENTS

| | | | |
|---|---|---|---|
| 7,140,845 B2 * | 11/2006 | Hsiao | 417/234 |
| 7,156,903 B2 * | 1/2007 | McCombs | 96/109 |
| 2001/0002592 A1 * | 6/2001 | Attolini | 128/200.21 |
| 2002/0005196 A1 * | 1/2002 | Brugger | 128/200.16 |
| 2003/0003003 A1 * | 1/2003 | Leonhard | 417/423.15 |
| 2004/0047744 A1 * | 3/2004 | Burkholder et al. | 417/234 |

* cited by examiner

AUTOMATISED ASSEMBLY OPERATING UNIT IN PARTICULAR FOR AEROSOL APPLIANCES

FIELD OF INVENTION

The invention concerns an operating unit, such as a pump or compressor integrated with a motor and a fan, usable in particular, but not exclusively, to generate a flow of air under pressure in aerosol therapy appliances.

STATE OF THE ART

The operating unit taken into consideration usually comprises a pump or compressor group with a relative head, an electric control motor and a fan for the motor. The pump group is placed in a body or shell and its head has an air inlet duct, an air outlet duct towards the user unit and at least one switch for starting and stopping the unit.

In the more traditional units, assembly of one such operating unit in the body or shell requires the provision of a series of passages for the air and wiring for the electric motor, operations to be carried out manually and which however prevent or at least hinder automizable assembly, that is to say, mechanised, of the group.

According to a previous patent for a utility model by the same applicant, the electric motor is integral with the pump or compressor and is assembled in the body or shell with the interposition of suspension elements, to damper and reduce vibration and noise. For this purpose, the motor is equipped with two supporting flanges, each one shaped to form two extensions facing in opposite directions, and at the ends of said extensions caps or damper bearings are applied which fit into corresponding seats inside the body or shell.

Even this innovative aspect, however, although improving the suspension system of the operating unit in the body, is not able to provide the conditions for automatizing the assembly of the group.

OBJECT AND SUMMARY OF THE INVENTION

Given the above premise, it is however the object of this invention to create the conditions, through a particular arrangement and combination of elements, so that assembly of the abovementioned type of operating unit is in fact automizable, that is to say mechanised, so as to reduce the use of labour, time and production costs.

Said object is achieved, according to the invention, with an operating unit to generate a flow of air under pressure in aerosol therapy equipment comprising a pump group that includes a head, and electric motor and a fan, a body that houses said pump group and is made up of two shells which overlap and join on a transversal plane by means of edges shaped to fit automatically one into the other, and where the head of the pump group has an inlet duct equipped with a filter and an air outlet duct, and the motor is equipped with suspension elements in said body and connected electrically to a power socket and to a switch supported by a plate with a fuse, characterised by the fact that the shells forming said body have means for receiving and holding the air inlet duct with filter, the air outlet duct and plate with fuse, power socket and switch, following their superimposition for an automated assembly of the group.

BRIEF DESCRIPTION OF THE DRAWINGS

Further details of the invention will be more apparent from the following description made in reference to the enclosed, indicative and non-limiting drawings, in which.

DETAILED DESCRIPTION OF THE INVENTION

Figure 1:
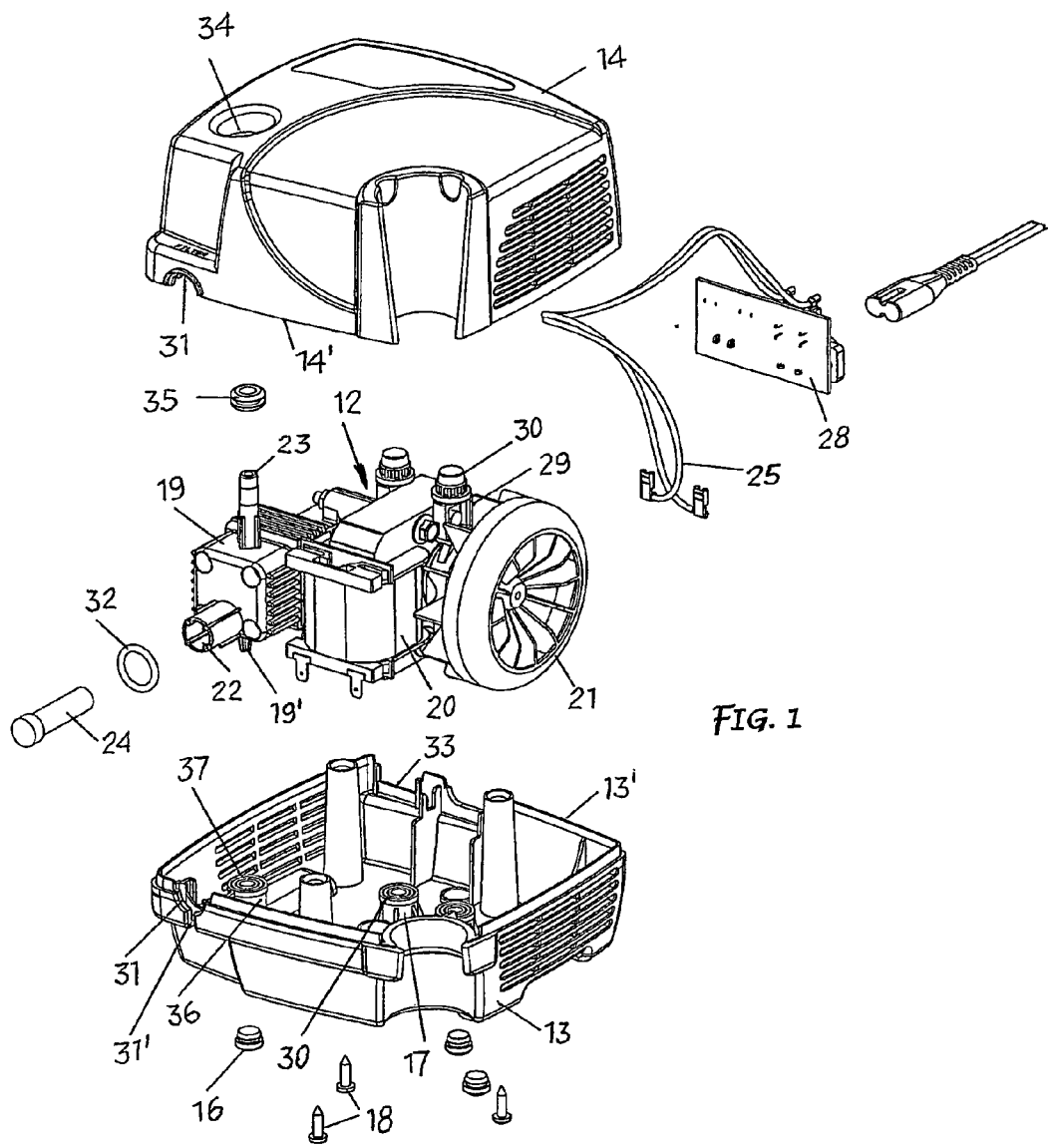
FIG. 1 shows an exploded view of the components of the operating unit.

As shown, the operating unit comprises fundamentally a body 11 and a pump group 12 enclosed in said body and designed to generate a flow of air under pressure.

The body 11 is made up of two elements or shells, one bottom 13 and one top 14, which superimpose and join on a transversal plane 15, at the level of their edges 13', 14' shaped to fit into each other, being self-centering. The bottom shell 13 is equipped with base legs 16. Internally both shells 13, 14, forming the body have seats 17 for assembling the pump group 12. The two shells 13, 14 are fixed to each other, for example, by means of screws 18 inserted through the bottom shell and engaging corresponding holes provided, although not shown, in the top shell. The two shells 13, 14, can also be fixed in some other way without changing the objective of the invention.

The pump group 12 has a head 19, and electric motor 20 and a fan 21 for the motor joined to form a group that does not require ducts to be provided but only electric power connection for the motor.

Figure 8:
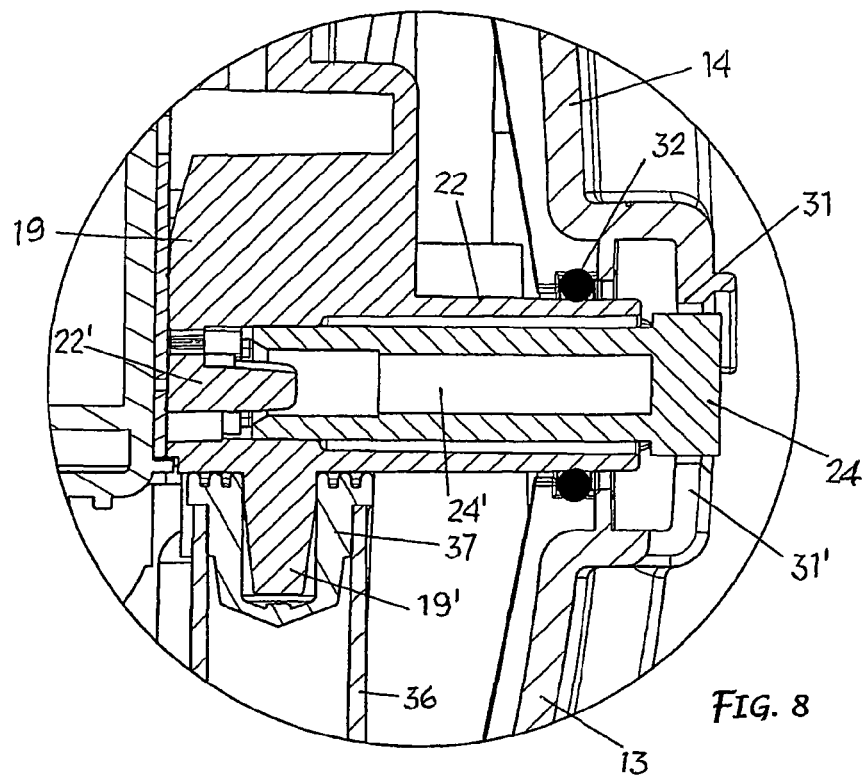
FIG. 8 shows an enlarged detail of FIG. 7 in correspondence with the air inlet duct with filter.

The head 19 of the pump group has an air inlet duct 22 and an outlet duct 23. In the air inlet duct 22 is positioned, for example, a polymeric filter 24 or some other type of material, which is interchangeable from the outside. The filter 24 is fitted tightly in the inlet channel 22 and has a longitudinal cavity 24", the internal end of which is associated with a pin 22' which partially occupies the cross section as shown in the detail in FIG. 8, with the advantage that it reduces noise.

The motor 20 is powered by means of electric cables 25, connected to a socket 26 and a switch 27 and a safety fuse—not shown—assembled on a plate 28. Furthermore, the motor has two supporting flanges each with two extensions 29 facing in opposite directions and which fit into corresponding seats 17 inside the two shells 13, 14 of the body or frame, each with interposition of a damper cap or bearing 30, as described in the abovementioned model of the same applicant.

In the example illustrated, the air inlet duct 22 protrudes from a lateral, vertical side of the head 19 of the pump group, whereas the air outlet duct 23 extends from the top horizontal side of said head 19, therefore at right angles to each other.

According to this arrangement, the mating edges 13', 14' of the two shells 13, 14 of the body 11 have, on one of their parts, two recesses, forming together, when the body is closed, a lateral seat 31 to receive the inlet duct 22 with interposition of a seal 32 and, in another of their parts, two slots to form, when the body is closed, a lateral opening 33 to receive and hold the socket, the switch and the plate with fuse for connecting the motor to the electric power supply. At the same time, the top shell 14 has a recess at the top with a hole 34 in the bottom to receive the air outlet duct 23, it also being fitted with a seal 35.

With the basic elements, that is to say the body 11 and the pump group 12, configured in this way, assembly of the operating unit can be carried out automatically using mechanical means, fundamentally as a pack—FIG. 1. This is carried out by positioning the group 12 in a first shell, placing the other shell on top of it so that, the air inlet duct 22 fits into its lateral seating 31, the socket and switch in the lateral opening 33 fits between the matching edges of the two shells and the air outlet 23 and relative seal in hole 34 at the top of the upper shell, and lastly by fixing the two shells together.

Figure 2:
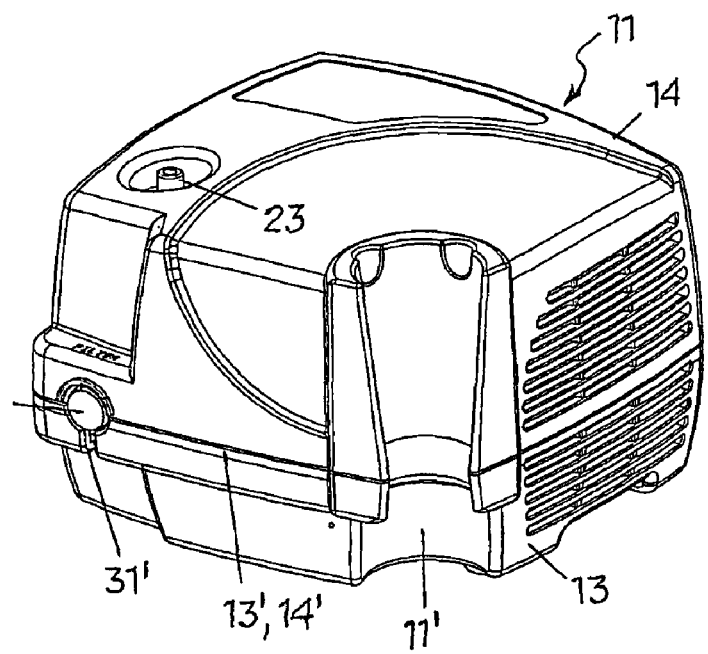
FIGS. 2 and 3 show two views in perspective from opposite sides of the assembled unit.
Figure 5:
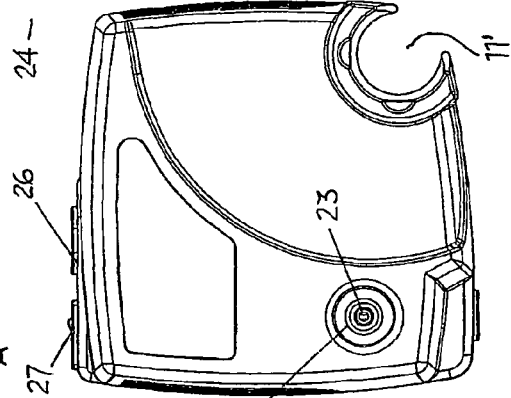
Figure 3:
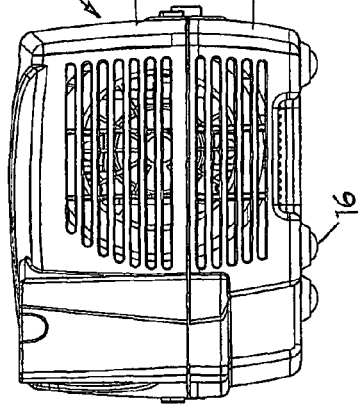
Figure 4:
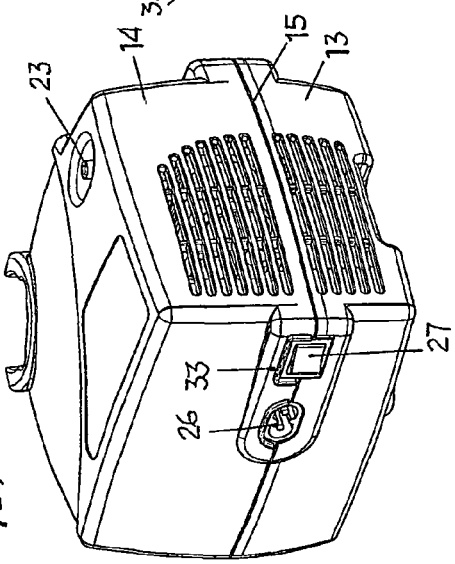
FIG. 4 shows a view from above of the unit in FIG. 2.

When the assembly has been effected, the air inlet duct 22 housing the filter 24 appears accessible on a side of the body—FIGS. 2 and 5—, the socket 26 and the switch 27 on another side of the body—FIG. 3—and the air outlet duct 23 on the top of the body itself—FIGS. 2 and 3—to insert an air delivery tube to the use facility. Filter 24 is, in this way, removable, operating from the outside of the body or shell by means of a tool to extract it through a slot 31' radially oriented to the seating 31 it is in.

Figure 7:
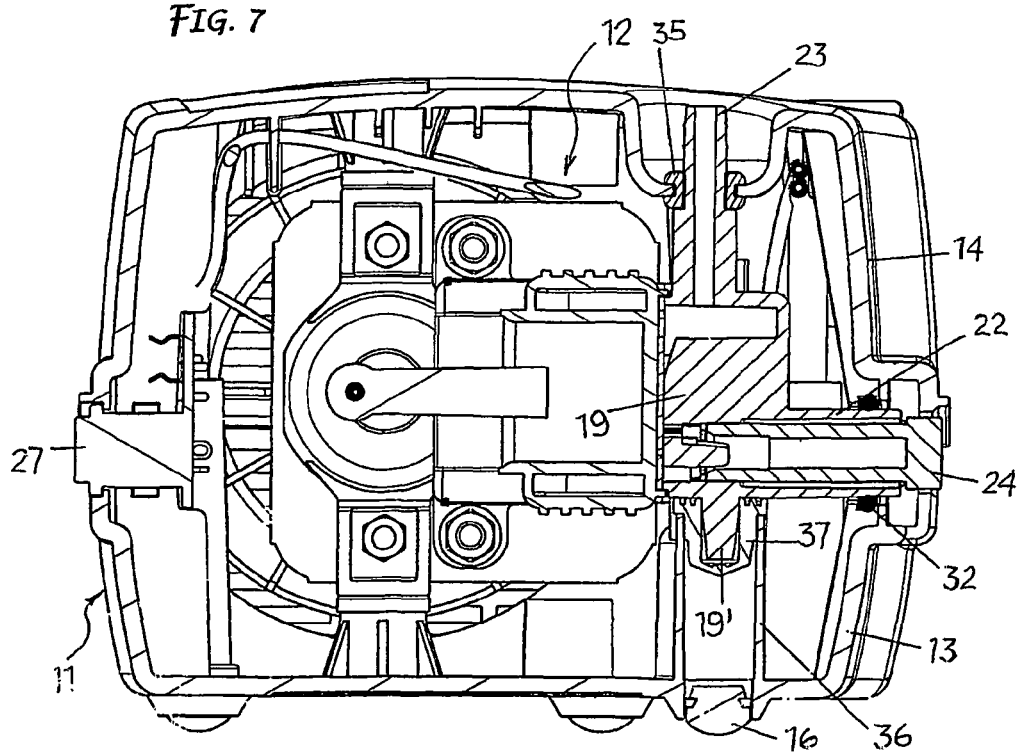
FIG. 7 shows an enlarged view of a cross-section according to arrows A-A in FIG. 5.

Of particular importance—FIGS. 1 and 7—is that inside the lower shell 13 of the body 11, on an axis with a foot on the base 16, there is a protrusion 36 acting as a support for the bottom part of the head 19 of the pump group 12. The protrusion 36 extends until it is up against the compressor or pump where it unites with a centering pin 19' with interposition of a damper element 37 and so as to be fundamentally in line and in front of the air outlet duct 23 in the top part—FIG. 7. This feature enables absorption, without causing any adverse effects, of the force applied on the outlet duct 23 when the air delivery tube to the use facility, is connected.

Differently from what has been described above, in a variation in the construction, where they are in right angle planes, the air input duct and output duct of the pump group can both be on the same horizontal plane and both be lodged between the matching edges of the shells forming the body when the latter is closed, or on a vertical plane and facing towards the top face of the body or shell, always and consequently with the possibility of automizable assembly of the group.

Figure 9:
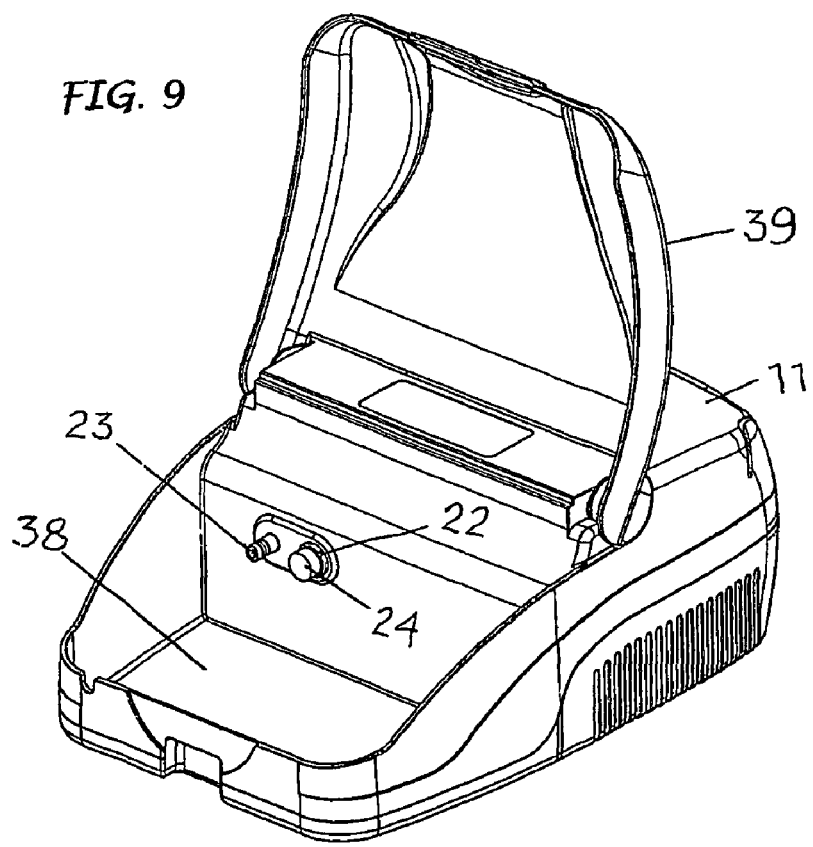
FIG. 9 shows a variation of the operating unit where the body has a tool holder compartment.
Figure 6:
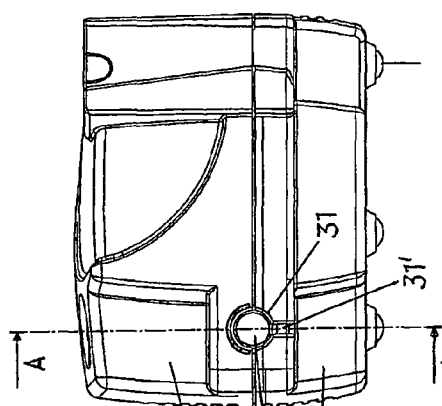
FIGS. 5 and 6 show two views from the front and side of the unit.

In a further embodiment such as the one shown in FIG. 9, the body 11 can be configured to form a tool holder compartment 38 closed by a cover 39, and the inlet 22 and outlet 23 air ducts of the pump group can be placed side by side across a wall of said compartment so as to be accessed through the latter.

The invention claimed is:

1. An operating unit to generate a flow of air under pressure in aerosol therapy appliances, the operating unit comprising:
   a pump group which includes a head, an electric motor and a fan; and
   a body enclosing said pump group and formed by a bottom shell and a top shell, said bottom shell having a bottom shell edge, said top shell having a top shell edge, one of said bottom shell and said top shell being superimposed on to the other one of said bottom shell and said top shell to close said body on a transversal plane, said transversal plane being on a level with said bottom shell edge and said top shell edge, said bottom shell edge and said top shell edge being formed to self-center one of said top shell and said bottom shell with the other one of said top shell and said bottom shell, said head having an air outlet duct and an air inlet duct comprising a filter, said electric motor comprising a plurality of suspension elements in said body and said electric motor being electrically connected to a socket and a switch supported by a plate with a fuse, said bottom shell and said top shell having means for receiving and holding the air inlet duct with said filter, the air outlet duct, and the plate with said fuse, said socket, and said switch following the overlapping of one of said top shell edge and said bottom shell edge with the other of the top shell edge and said bottom shell edge upon an automated assembly of said pump group with said body, wherein each of said top shell and said bottom shell has a first recess and a slot, said first recess and said slot of said top shell being on a level with said top shell edge, said first recess and said slot of said bottom shell being on a level with said bottom shell edge, said top shell edge being aligned with said bottom shell edge, said means for receiving and holding said air inlet duct with said filter being provided by said first recess of said top shell joined with said first recess of said second shell when said body is closed to form a lateral lodging to receive the air inlet duct and the air filter, said means for receiving and holding the socket, the switch, and the plate comprising said slot of said top shell and said slot of said bottom shell, said slot of said top shell being joined with said slot of said bottom shell when said body is closed to form a lateral opening that receives and holds said socket, said switch, and said plate for connecting said electric motor to an electric supply source, said means for receiving and holding said outlet duct comprising a second recess on a top surface of said top shell, said second recess receiving said air outlet duct.

2. Operating unit according to claim 1, wherein the air inlet duct and the air outlet duct of the pump group are in planes at right angles to each other.

3. Operating unit according to claim 1, wherein said means for receiving and holding the air inlet duct further comprises a first seal arranged between said air inlet duct and said first recess in said top shell and said first recess in said bottom shell, and said means for receiving and holding the air outlet duct further comprises a second seal is arranged between said air outlet duct and said second recess.

4. Operating unit according to claim 1, wherein a bottom portion of said bottom shell of said body is equipped with a plurality of feet, wherein a protrusion is disposed inside said bottom shell on an axis with one of said feet, said protrusion acting as a support for the head of the pump group, said protrusion extending to rest against a bottom part of said head, said protrusion being aligned with said air outlet duct and said protrusion facing said air outlet duct, wherein a damper element is arranged between said bottom part of said head and said protrusion.

5. Operating unit according to claim 1, wherein said filter is tightly fitted in the air inlet duct and has a longitudinal cavity partially obstructed by a pin.

6. Operating unit according to claim 1, wherein said filter can be removed from the outside of the body, said filter being accessible using a tool to remove said filter through a filter slot provided in said body and radially oriented to said means for holding and receiving said air inlet duct.

7. An operating unit to generate a flow of air under pressure in aerosol therapy appliances, the operating unit comprising:
   a pump group which includes a head, an electric motor and a fan; and
   a body enclosing said pump group and formed by a bottom shell and a top shell, said bottom shell having a bottom shell edge, said top shell having a top shell edge, one of said bottom shell and said top shell being superimposed on to the other one of said bottom shell and said top shell to close said body on a transversal plane, said transversal plane being on a level with said bottom shell edge and said top shell edge, said bottom shell edge and said top shell edge being formed to self-center one of said top shell and said bottom shell with the other one of said top shell and said bottom shell, said head having an air inlet duct comprising a filter and an air outlet duct, said electric motor comprising a plurality of suspension elements in said body and said electric motor being electrically connected to a socket and a switch supported by a plate with a fuse, said bottom shell and said top shell having means for receiving and holding the air inlet duct with said filter, the air outlet duct, and the plate with said fuse, said socket, and said switch following the overlapping of one of said top shell edge and said bottom shell edge with the other of the top shell edge and said bottom shell edge upon an automated assembly of said pump group with said body, wherein said means for receiving and holding said air inlet duct with said filter is provided by a side seating in which the air inlet duct with filter is lodged, said side seating being formed by a first recess in said top shell and a first recess in said bottom shell, wherein said means for receiving and holding said air inlet duct with said filter further comprises a first seal arranged between said air inlet duct and said first recess in said top shell and said first recess in said bottom shell, wherein said means for receiving and holding the air outlet duct is provided by a second seal arranged between said air outlet duct and a hole defined by a second recess in a top portion of the top shell, wherein said air outlet duct is arranged in said hole in said top shell.

8. An operating unit to generate a flow of air under pressure in aerosol therapy appliances, the operating unit comprising:

a pump group which includes a head, an electric motor and a fan; and a body enclosing said pump group and formed by a bottom shell and a top shell, said bottom shell having a bottom shell edge, said top shell having a top shell edge, one of said bottom shell and said top shell being superimposed on to the other one of said bottom shell and said top shell to close said body on a transversal plane, said transversal plane being on a level with said bottom shell edge and said top shell edge, said bottom shell edge and said top shell edge being formed to self-center one of said top shell and said bottom shell with the other one of said top shell and said bottom shell, said head having an air inlet duct comprising a filter and an air outlet duct, said electric motor comprising a plurality of suspension elements in said body and said electric motor being electrically connected to a socket and a switch supported by a plate with a fuse, said bottom shell and said top shell having means for receiving and holding the air inlet duct with said filter, the air outlet duct, and the plate with said fuse, said socket, and said switch following the overlapping of one of said top shell edge and said bottom shell edge with the other of the top shell edge and said bottom shell edge upon an automated assembly of said pump group with said body, wherein a bottom portion of said bottom shell of said body is equipped with a plurality of feet, wherein a protrusion is disposed inside said bottom shell on an axis with one of said feet, said protrusion acting as a support for the head of the pump group, said protrusion extending to rest against a bottom part of said head, said protrusion being aligned with said air outlet duct and said protrusion facing said air outlet duct, wherein a damper element is arranged between said bottom part of said head and said protrusion.

* * * * *